United States Patent
Kruger et al.

(10) Patent No.: US 9,349,573 B2
(45) Date of Patent: May 24, 2016

(54) TOTAL RELEASE METHOD FOR SAMPLE EXTRACTION IN AN ENERGETIC-BEAM INSTRUMENT

(71) Applicant: Oxford Instruments Nanotechnology Tools Limited, Oxon (GB)

(72) Inventors: Rocky Kruger, Point, TX (US); Gonzalo Amador, Dallas, TX (US); Cheryl Hartfield, Plano, TX (US)

(73) Assignee: Omniprobe, Inc., Dallas, TX (US)

( * ) Notice: Subject to any disclaimer, the term of this patent is extended or adjusted under 35 U.S.C. 154(b) by 0 days.

(21) Appl. No.: 14/797,087

(22) Filed: Jul. 11, 2015

(65) Prior Publication Data

US 2016/0035540 A1 Feb. 4, 2016

Related U.S. Application Data

(60) Provisional application No. 62/031,959, filed on Aug. 1, 2014.

(51) Int. Cl.
*G01N 1/28* (2006.01)
*H01J 37/31* (2006.01)
*H01J 37/20* (2006.01)
*H01J 37/26* (2006.01)

(52) U.S. Cl.
CPC . *H01J 37/31* (2013.01); *G01N 1/28* (2013.01); *H01J 37/20* (2013.01); *H01J 37/261* (2013.01); *H01J 2237/2007* (2013.01); *H01J 2237/2802* (2013.01); *H01J 2237/31749* (2013.01)

(58) Field of Classification Search
USPC .......................................... 250/304, 307, 311
See application file for complete search history.

(56) References Cited

U.S. PATENT DOCUMENTS

| | | | |
|---|---|---|---|
| 5,270,552 A | 12/1993 | Ohnishi | |
| 6,570,170 B2 | 5/2003 | Moore | |
| 7,180,061 B2 | 2/2007 | Lu | |
| 7,317,188 B2 | 1/2008 | Zhang | |
| 7,375,325 B2 | 5/2008 | Burkhardt | |
| 8,134,124 B2 * | 3/2012 | Blackwood | G01N 1/32 250/304 |
| 8,143,594 B2 | 3/2012 | Wanzenboeck | |
| 2015/0028225 A1 | 1/2015 | Lechner | |

OTHER PUBLICATIONS

Engelmann, H.J., Challenges to TEM in high performance microprocessor manufacturing, EMC 2008 14th European Microscopy Congress Sep. 1-5, 2008, Aachen, Germany, pp. 13-14.

* cited by examiner

*Primary Examiner* — Kiet T Nguyen
(74) *Attorney, Agent, or Firm* — John A. Thomas

(57) ABSTRACT

A substrate located in an energetic-beam instrument has a region of interest to be extracted as a sample for further analysis. Cuts are made in the substrate to define a sample, and a stress-buffer layer is formed over the region of interest or adjacent to it. An isolating cut is made to separate the portion of the substrate containing the region of interest from the bulk substrate; however, the isolated area remains attached to the stress-buffer layer. An end-effector, such as the probe of a nano-manipulator, is attached to the stress-buffer layer, and the stress-buffer layer is cut to free the sample. The sample may then be attached to a holder by attachment of the stress-buffer layer thereto. Thus the sample is never at the same time connected directly and rigidly to two different objects that may move relatively to one another, creating undesirable stresses in the sample.

21 Claims, 8 Drawing Sheets

TOTAL RELEASE METHOD FOR SAMPLE EXTRACTION IN AN ENERGETIC-BEAM INSTRUMENT

CLAIM FOR PRIORITY

This application claims the priority of U.S. Provisional Patent Application, Ser. No. 62/031,959, filed Aug. 1, 2014, which application is incorporated in its entirety by reference into the present application.

BACKGROUND

1. Technical Field

The present disclosure describes methods for separating a sample from a substrate, and particularly relates to a method for separating a small sample region from a substrate such as a semiconductor wafer in an energetic-beam instrument.

2. Background

Certain inspection methods of samples from integrated circuit wafers and other materials require the fabrication of an electron-transparent (<50 nm thickness) area on the sample that contains the region of interest for observation. Typically, a sample is cut out of a semiconductor wafer or other object by use of an energetic-beam instrument such as a focused-ion beam microscope (FIB) for further processing, modification, or analysis; and analyzed or imaged, if desired, using a transmission electron microscope (TEM), scanning electron microscope (SEM), or other means.

Some definitions of terminology in this application follow. The "substrate" need not be a semiconductor device. It may, for example, be a micromechanical device, or any solid substance whatever requiring TEM. SEM, atom-probe, or other analysis, such as particles, granules, biological materials, or thin films. The "energetic-beam instrument" may be either a single-beam FIB, or a multi-beam FIB; the latter having both an ion beam and an electron beam, and possibly also a laser. Typical energetic-beam beam instruments are those manufactured by Carl Zeiss, Inc. of Oberkochen, Germany or FEI Company of Hillsboro, Oreg. An "end-effector" is a component that can manipulate a sample in vacuum when connected to a nano-manipulator; the nano-manipulator being connected to the energetic-beam instrument with vacuum feedthrough. The end-effector may be a simply a fine probe or a micro-gripper device. Most illustrations of the disclosed method in this application refer to a probe, but the method disclosed is not limited to cases where a probe is the end-effector. A suitable nano-manipulator is the OMNIPROBE® 200, manufactured by Oxford Instruments, Omniprobe Products, Dallas, Tex. A "cut" with the energetic-beam is a completed cut as here illustrated or described, which "cut" may actually comprise a series of smaller discrete cuts made in the pattern of the completed cut illustrated or described. The terms "first" and "second" as modifiers to distinguish two objects or procedures do not imply a sequence in time unless so stated.

In situ lift-out is a method for performing the entire TEM sample preparation within the vacuum chamber of an energetic-beam instrument. It relies on a manipulator holding an end-effector of some sort. Often, in situ lift-out uses the gas-assisted material deposition capability, or chemical-vapor deposition (CVD) capability of the energetic-beam instrument to connect the excised sample containing the region of interest to the tip of a probe. Alternatively, the sample may be pierced by the probe tip, or clasped by micro-grippers or clamps. The excised sample can then be attached to a TEM grid or other holder by means of gas-assisted material deposition. After the sample has been welded to a probe tip by FIB gas-assisted deposition, the separation of the sample from the probe is made by applying the energetic-beam (generally the ion beam) to sever the connection. In any case, the region of interest can be thinned to an electron-transparent thickness using ion milling. In a previously practiced method for in situ lift-out (U.S. Pat. No. 5,270,552 to Ohnishi, et al.), the tip of the probe is connected to a partially excised sample before the sample is completely released from the wafer. This practice has disadvantages overcome in the present disclosure.

There is always a danger that transient mechanical forces can be transmitted to the sample while it is attached to an end-effector and simultaneously to a second object, such as the substrate or TEM grid. For example, shocks can be initiated by movement of mechanical actuators controlling gas injection, causing relative displacement between the probe and sample, or thermal or mechanical drift of either the end-effector or the stage supporting the sample may occur. Forces arising from the relative displacement caused by these events can change the natural strain state of the material and induce artifacts such as dislocations. In severe instances, fractures and cracks are created.

Prior-art methods share at least one step somewhere in the workflow where a lift-out sample is simultaneously attached to two objects. An example is when an end-effector attaches to a partially excised lift-out sample before its full release from the substrate. Another case occurs after completing the lift-out, where the excised sample is attached to a holder or support while still held by the end-effector.

An important goal of any sample preparation method is the avoidance of creating artifacts in the sample. There is a need for an in situ lift-out method that avoids the danger of damaging a sample or inducing artifacts during lift-out and any following steps, and that also minimizes the time during which a transient mechanical event can place damaging stress on the end-effector and sample or cause unacceptable delays.

DRAWINGS

Non-limiting embodiments of the present disclosure are described by way of example in the accompanying drawings, which are schematic and are not intended to be drawn to scale.

SUMMARY

We disclose a method for sample separation and lift-out comprising positioning a substrate having a region of interest to be lifted out inside an energetic-beam instrument. A stress-buffer layer is applied over the region of interest (or in some embodiments, adjacent to it), extending in at least one dimension past the region of interest. A first cut with the energetic beam is made into the substrate on at least one side of the region of interest, and a second cut with the energetic beam is made into the substrate on an opposite side of the region of interest, thus defining a lamella or lift-out sample to be isolated. In some embodiments, a wedge-shaped sample is defined by the second cut. The third cut of a lamella sample, or the second cut of the wedge-shaped sample, is an isolating cut made with the energetic beam to form a lift-out sample containing the region of interest, so that the sample remains attached to the stress-buffer layer, but is otherwise freed from the substrate, while the stress-buffer layer is still in contact with the substrate in at least one extended dimension. In this way, the method disclosed here avoids the situations in the prior art where weld material directly and rigidly connects the lift-out sample to the end-effector while it is still directly attached to its bulk substrate, and when the excised lift-out sample is simultaneously welded to a holder or grid. In this new method, the sample is never at the same time connected directly and rigidly to two different objects that may move relative to one another, thus avoiding the risk of stress or fracture of the sample.

An end-effector is connected to the stress-buffer layer, and the portion of the stress-buffer layer holding the isolated sample to the substrate is completely severed, freeing the sample for lift-out from the substrate. The end-effector may be connected to the stress-buffer layer directly over the excised sample, or to one or the other side thereof, depending on the sensitivity of the material in the sample to different stress modes. In other embodiments, the isolating cut may extend at least partially into the stress-buffer layer.

DETAILED DESCRIPTION

Figure 1:
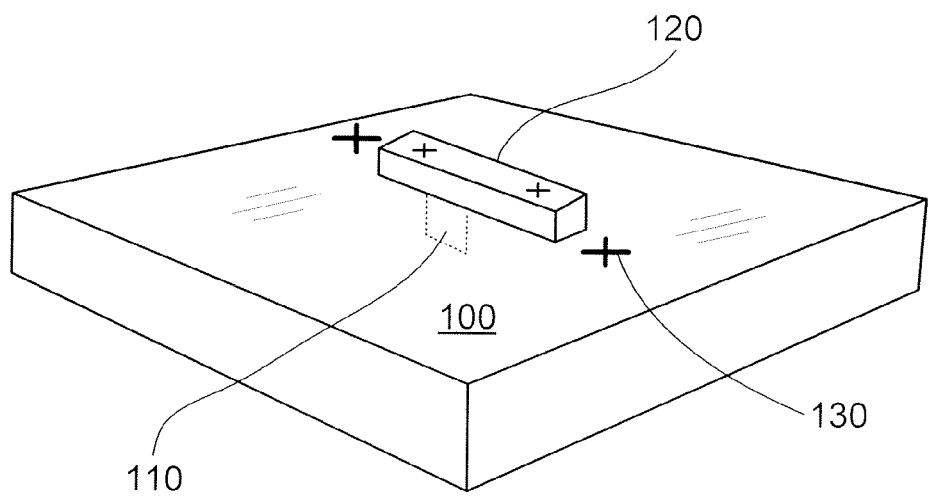
FIG. 1 shows a substrate having a region of interest for extraction. A stress-buffer layer is formed over the region of interest.

FIG. 1 shows schematically a substrate 100 containing a region of interest 110. A gas-injection system (not shown) has laid down a stress-buffer layer 120 over the region of interest 110. FIG. 1 also shows optional alignment marks 130 that may be milled into the surface of the substrate 100 or the stress-buffer layer 120, or both.

The material for the stress-buffer layer should be chosen based on its having sufficient mechanical properties to reduce mechanical stresses applied to the sample during nano-manipulation operations. In contrast, the standard energetic beam-assisted CVD protective layers that are deposited are chosen based primarily on properties of having low ion sputtering rates so as to serve as hard masks protecting the sample during ion milling, and secondarily, based on material properties providing sufficient imaging contrast to the sample in the TEM and having suitable properties of amorphous or very fine crystalline structure to reduce curtaining artifacts.

The deposited material used for the stress-buffer layer should be a material that does not fracture in a brittle manner when a crack is present, since this could result in the catastrophic loss of the sample (assuming perfect bonds between the stress-buffer layer and the sample surface). No matter how high the fracture strength of a brittle attachment material, the likelihood of very high leveraged stresses at the point of contact between the probe tip and sample, and the risk of damaging mechanical shock and vibration from the microscope and environment, make the selection of a brittle material unwise.

Lift-out failures causing sample damage or loss are typically due to mechanical stresses transmitted at the contact point between the end-effector and the sample. Often the fail site occurs at the vicinity of the weld between the end effector and sample. Therefore the ideal stress-buffer material would deform at a lower stress level than that sufficient to cause the weld to fail. It should possess the desired mechanical property of high fracture toughness. Materials with high fracture toughness absorb a larger amount of energy before failing and are more likely to fail by ductile fracture. Although plastic deformation of the stress-buffer material may result in some misalignment of the sample, this would be preferred to the loss of the sample. As long as the misalignment is not too severe, it can most likely be corrected for, either by reorientation of the sample or by mechanical realignment. The selection of the stress-buffer material should provide for sufficient fracture toughness with an appropriate stiffness (resistance to deformation). A material such as a CVD conductive polymer would likely be a good candidate for this application.

Other suitable materials include pure metals, such as Au and Pt, as well as high fracture strength brittle materials that behave elastically in thin films and that are not heavily contaminated with byproducts of the deposition process. It may be necessary to perform tests of deposited CVD materials to determine the actual mechanical properties of these films for suitability to their role as a stress-buffer layer in this application. Pure metals may be deposited by methods known in the art, such as those described in: Roberts, Nicholas A. et al. "Enhanced material purity and resolution via synchronized laser assisted electron beam induced deposition of platinum," Nanoscale 5.1 (2013): 408-415.

It should be noted that the desired stress-buffer layer 120 may in some cases be provided by the conventional practice of depositing a protective layer over the region of interest 110. The purpose of the protective layer is to protect the sample surface from erosion by the energetic beam during sample processing and imaging. Typically this protective layer is platinum, deposited by a precursor from a gas-injection system (not shown). Carbon and oxide protective layers are often used, but would not have sufficient ductility for stress mitigation. We can take advantage of a platinum protective layer itself as a stress-buffer layer 120 by extending it in at least one dimension beyond the area that will be extracted during lift-out, or by applying it in addition to a protective layer such as carbon. We have found that a stress-buffer layer 120 should be approximately 2 to 3 μm thick for best results with the methods disclosed here. FIG. 1 shows the stress-buffer layer as parallelepiped, but it may be any suitable arbitrary shape, so long as it extends over both the region of interest 110 and the substrate 100 in at least one dimension after the desired sample 170 is isolated, as next described.

Figure 2:
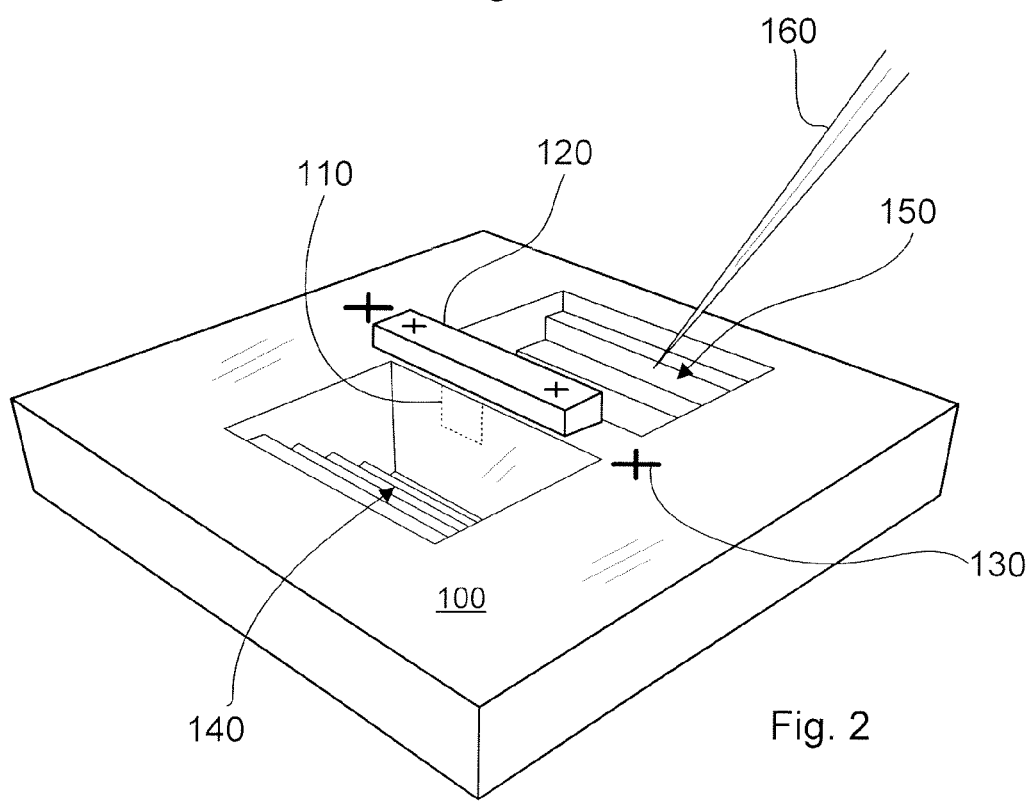
FIG. 2 shows the substrate milled away from the region of interest.

After laying-down of the stress-buffer layer 120, a first trench 140 is formed in the front side of the region of interest 110, and a second trench 150 is formed on the back side of the region of interest, as shown in FIG. 2. The first trench 140 and the second trench 150 may be formed by milling with the focused ion-beam 160, as is known in the art. The substrate 100 may be tilted in the FIB as necessary to accomplish the milling of the trenches 140, 150. The milled trenches 140, 150 on either side of the stress-buffer layer 120 do not need to be equal in size. However, one side needs to be large enough to access the desired area for cutting out the sample 170, as shown in FIG. 3.

Figure 3:
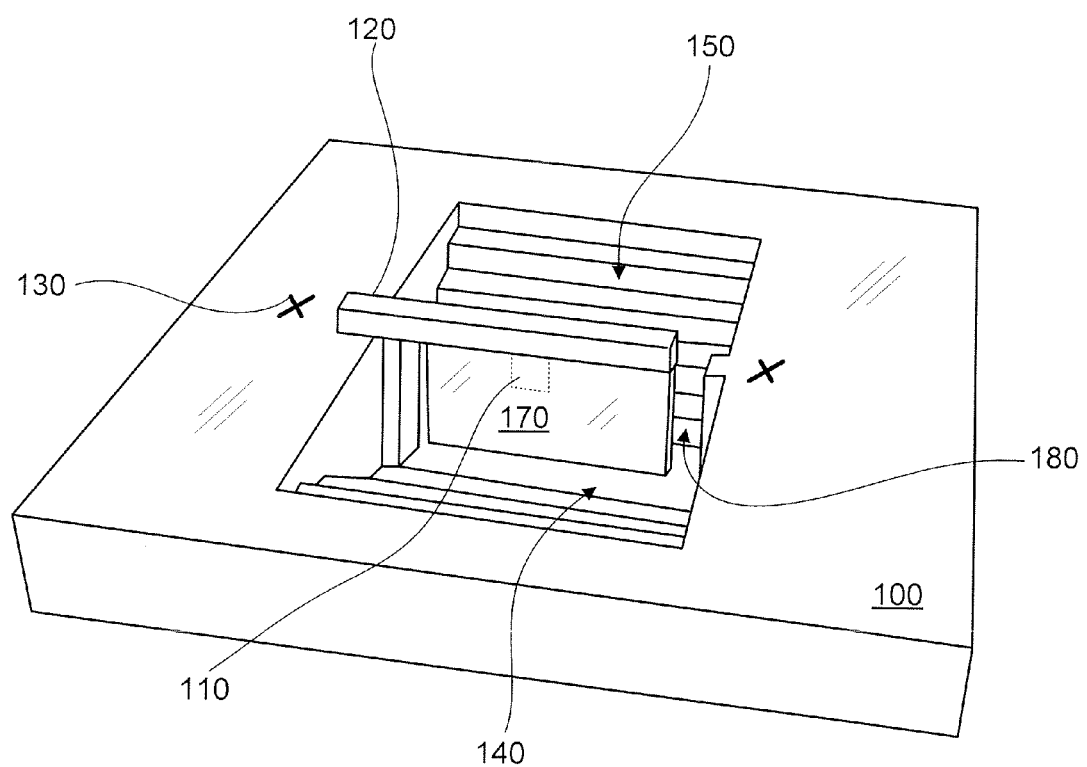
FIG. 3 shows the desired sample, or lamella, isolated from the substrate by milling operations.

FIG. 3 shows the next milling operation completed, where the sample 170 containing the region of interest 110 is isolated from the substrate 100 by an isolating cut 180, so that the sample 170 is completely isolated from the bulk substrate 100, although still attached to the stress-buffer layer 120. In this way, attachment of an end-effector, illustrated hereafter by the probe 190 of a nano-manipulator, is made only on the stress-buffer layer 120, and not the sample 170 itself. The reader should note that the region of interest 110 depicted schematically in the drawings may actually include the entire sample 170, and is not necessarily restricted to a small area within the sample 170, as suggested by the drawings.

Figure 4A:
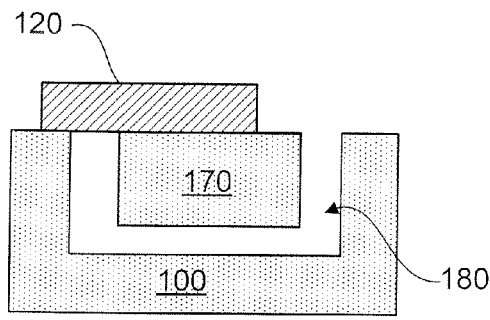
FIGS. 4A through 4F show different embodiments of operations to isolate the sample containing the region of interest from the substrate.
Figure 4B:
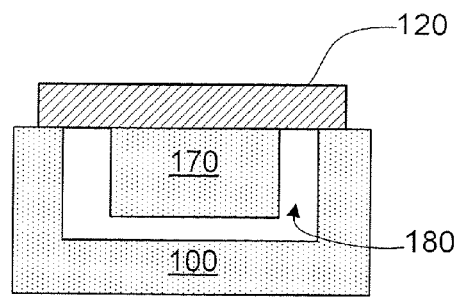
Figure 4C:
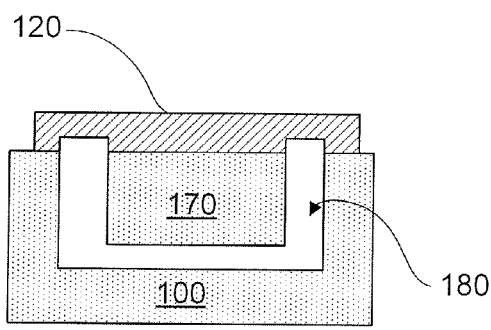
Figure 4D:
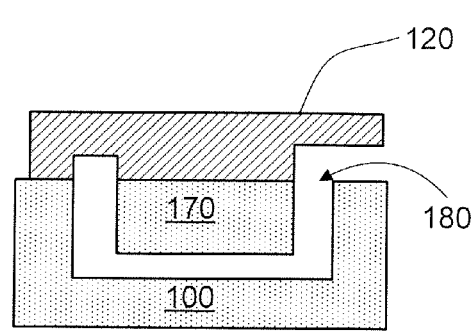
Figure 4E:
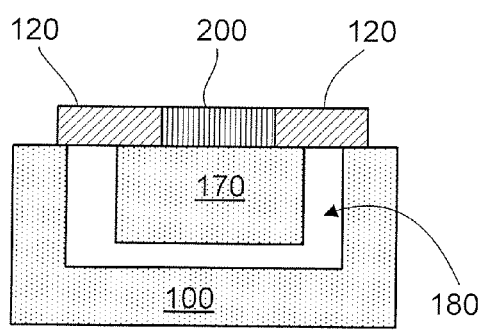
Figure 4F:
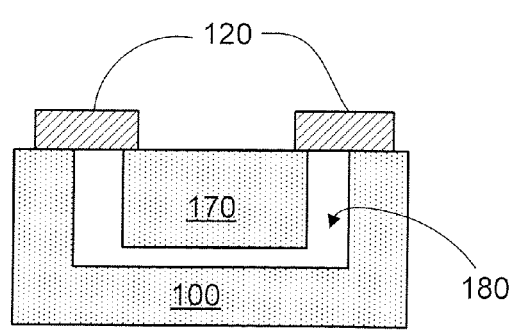

FIGS. 4A through 4 show schematically embodiments of the isolating cut 180 operation, isolating the sample 170 from the substrate 100. FIG. 4A shows the isolating cut 180 isolating a sample 170 held on one side to the substrate 100 by the stress-buffer layer 120. FIG. 4B shows a stress-buffer layer 120 extending over both edges of an isolated sample 170. FIG. 4C shows the same configuration as 4B, but here the isolating cut 180 has removed some material from the stress-butter layer 120. FIG. 4D shows the same configuration as FIG. 4C, but here the isolating cut 180 has released one side of the stress-buffer layer 120. FIG. 4E represents a stress-buffer layer 120 on either side of the isolating cut 180, and illustrates that a different protective layer 200, such as carbon, not suitable for stress-buffering, may be formed over the region of interest 110, so long as an appropriate stress-buffer layer 120 bridges the gap between the sample 170 and the substrate 100. FIG. 4F shows a sample 170 without a protective layer or any stress-buffer layer 120 directly over the region of interest 110. In the foregoing illustrations, the isolating cut 180 is shown as U-shaped, but any arbitrary shape may be used, so long as it isolates the sample 170 from the substrate 100 as shown. Also, the reader should note that the stress-buffer layer 120 may be laid down after a cut is made to partially isolate the sample 170, but before completing the isolating cut 180 to completely isolate the sample 170.

Figure 5A:
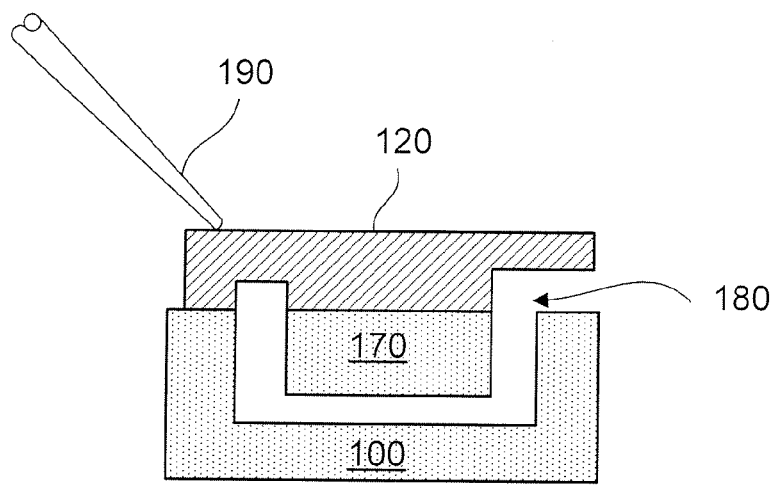
FIGS. 5A through 5C show different embodiments of end-effector placement (in this case a probe) on the stress-buffer layer.
Figure 5B:
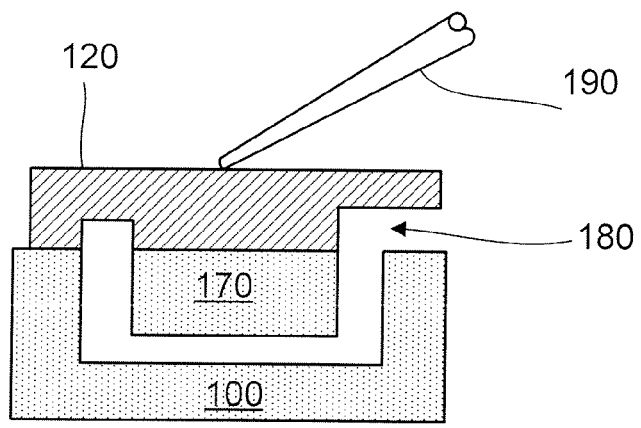
Figure 5C:
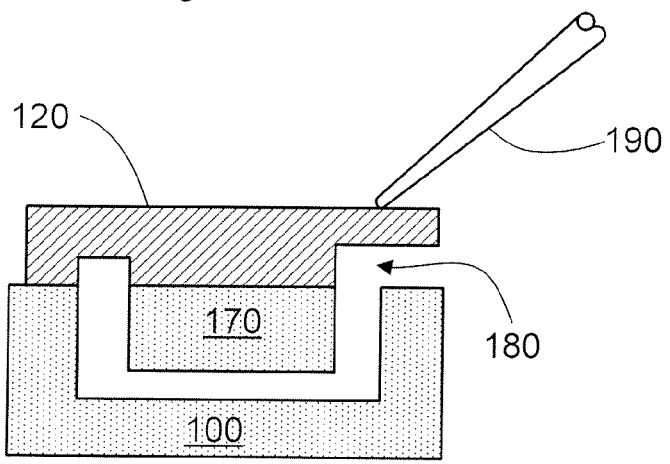

FIGS. 5A through 5B shown possible attachments of an end-effector, in this case a probe 190, to an exemplary stress-buffer layer 120; respectively, from one side, or the center, or the opposing side of the stress-buffer layer 120, depending on the sensitivity of the substrate 100 material to tensile versus mixed-mode stresses, or depending on geometric access of the probe 190 to the sample 170. For clarity, the region of interest 110 in the sample 170 is not shown in these drawings.

Figure 6:
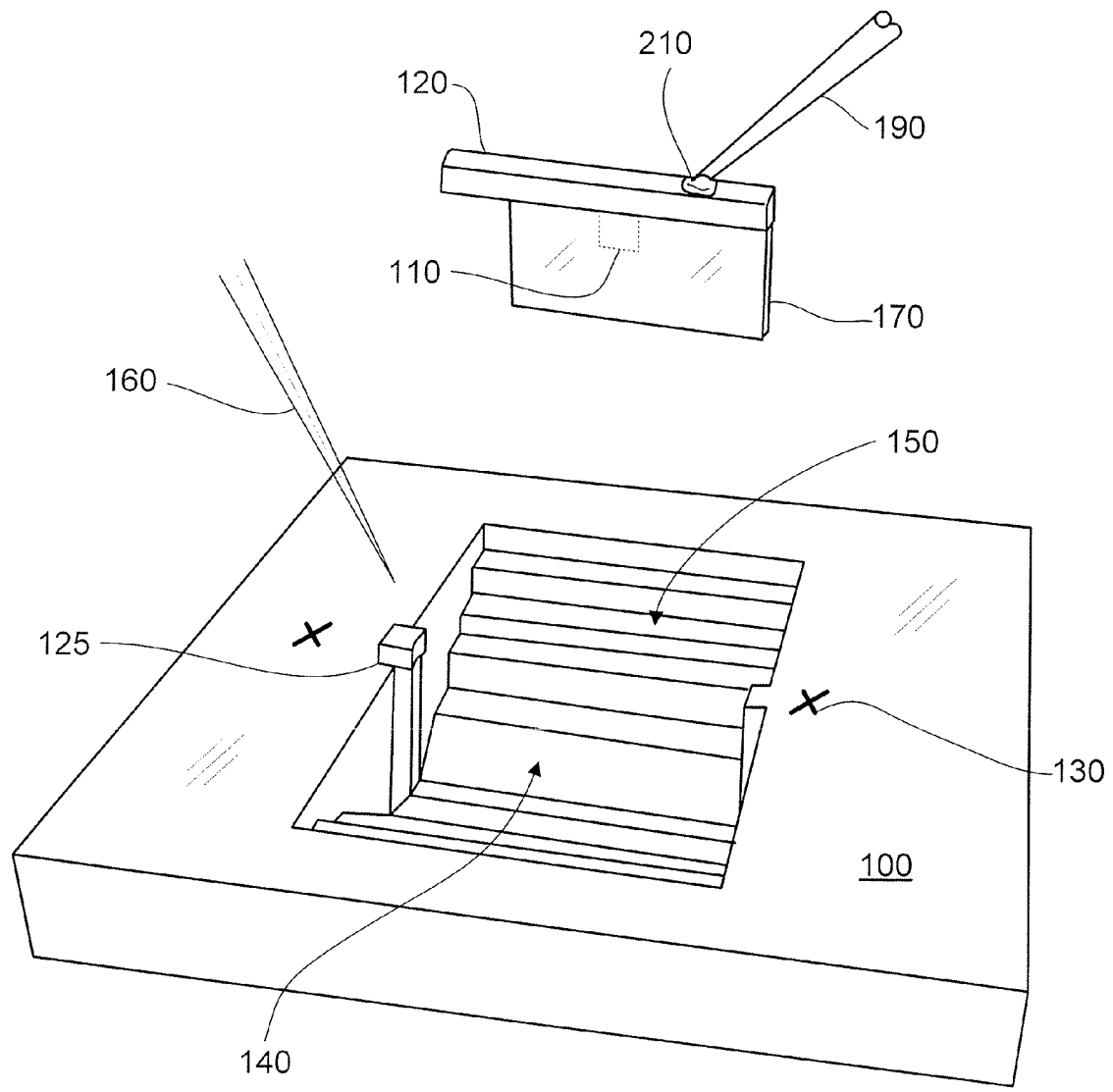
FIG. 6 shows the sample extracted from the substrate.

FIG. 6 shows lift-out of the isolated sample 170 from the substrate 100 after cutting of the stress-buffer layer 120 with an energetic beam 160. Note that the cutting of the stress-buffer layer 120 has left a remnant 125 of the stress-buffer layer 120 still attached to the substrate 100, as would typically be the case. In FIG. 6, the probe 190 is shown attached to the stress-buffer layer 120 by CVD welding 210, although other methods known in the art may be used. Lift-out from the vicinity of the substrate 100 may be accomplished in conventional ways, such as by lowering the stage supporting the substrate 100.

Figure 7A:
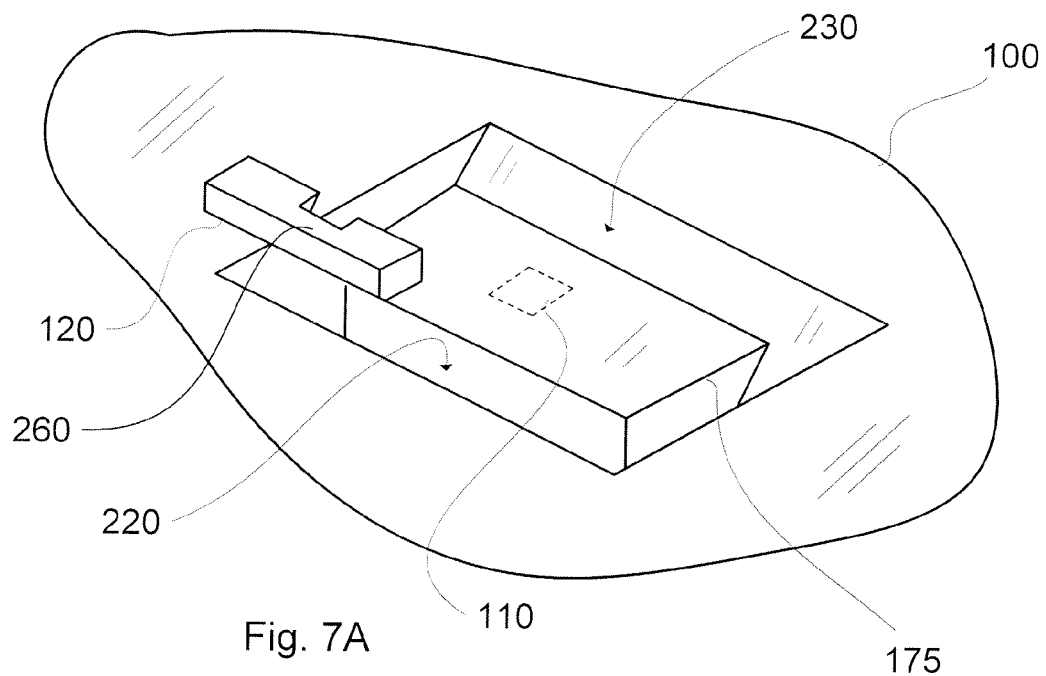
FIGS. 7A and 7B show an alternative embodiment, for the extraction of a wedge-shaped sample.
Figure 7B:
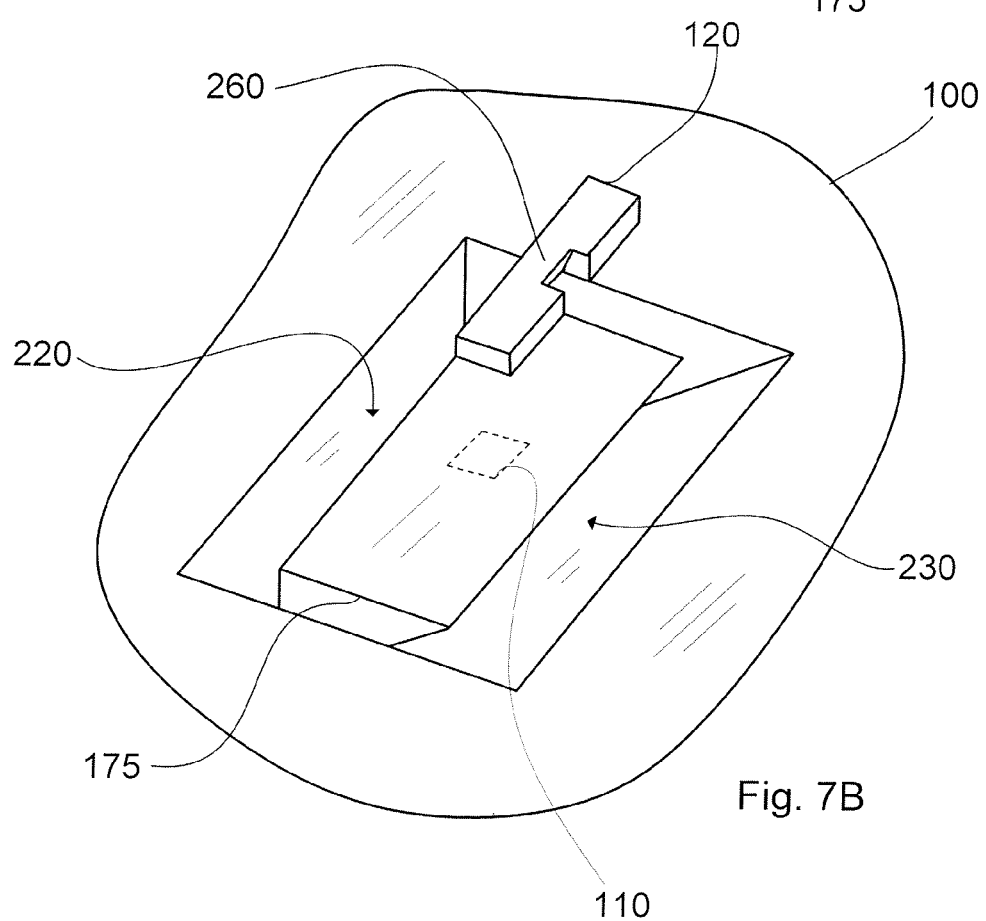

FIGS. 7A and 7B illustrate a different embodiment, where a wedge-shaped sample 175 is isolated from the substrate 100 with a first cut 220 and a second cut 230. A stress-buffer layer 120, shown in the shape of a bar here, and having a known minimum height, is laid down at least partially over the area of the sample 175 to be extracted, before the second cut 230. The second cut 230 is the isolating cut, where the wedge-shaped sample 175 comprising the region of interest 110 is freed from the substrate 100, but still attached to the stress-buffer layer 120. The first cut 220 is made at substantially normal incidence to the plane of the substrate. The second cut 230 is made at an angle of less than 90 degrees, preferably about 45-60 degrees, to the plane of the substrate. The second cut 230 thus undercuts the sample 175 and isolates it from the substrate 100, but is calculated so as to cut into, but not through, the stress-buffer layer 120.

Techniques for the release of a wedge-shaped sample 175 by such cuts are disclosed in U.S. Pat. No. 6,570,170, titled "Total release method for sample extraction from a charged-particle instrument," which patent is incorporated by reference in its entirety into the present application.

Figure 8:
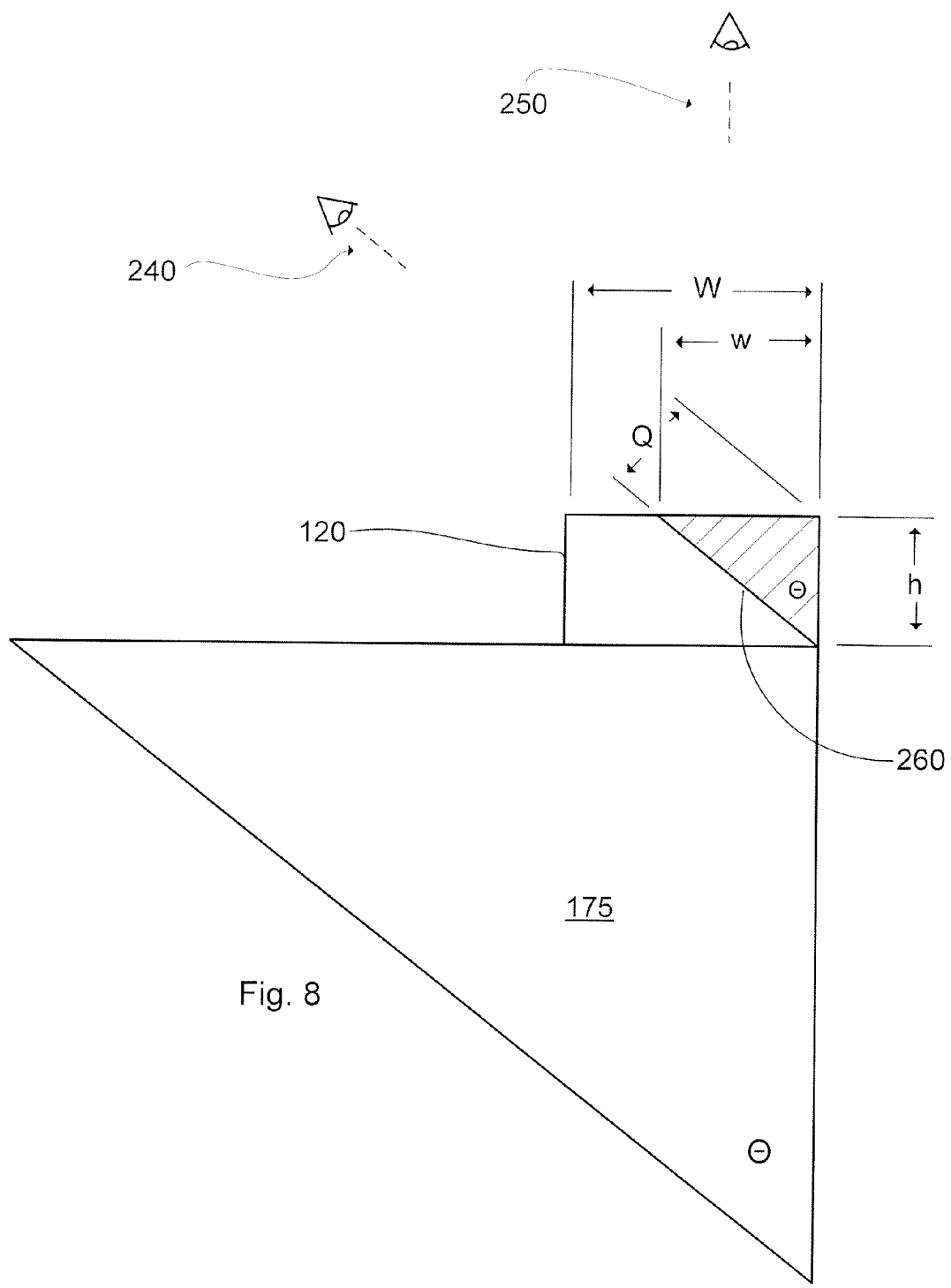
FIG. 8 illustrates calculations for the location of an isolating cut in the embodiment shown in FIGS. 7A and 7B.

FIG. 8 shows a particular method for conveniently calculating the dimensions of the second cut 230, so that the sample 175 is freed from the substrate 100, but the second cut 230 is not made completely through the stress-buffer layer 120, thus leaving a connecting portion 260 that is severed when the sample 175 is lifted-out, as described previously. The ion-beam view 240 and the electron-beam view 250 in the energetic-beam instrument are shown. In FIG. 8, the projected width of the connecting portion 260 of the stress-relief buffer 120 after the second cut 230 is calculated from the following parameters:

W=width of the stress-relief buffer 120
h=height of stress-relief buffer 120
w=width of connecting portion 260 of stress-relief buffer after second cut 230
$\Theta$=angle between e-beam axis and ion-beam axis minus stage-tilt angle
Q=projected width of w from the ion-beam view 240, thus Q=h sin($\Theta$)

Figure 9:
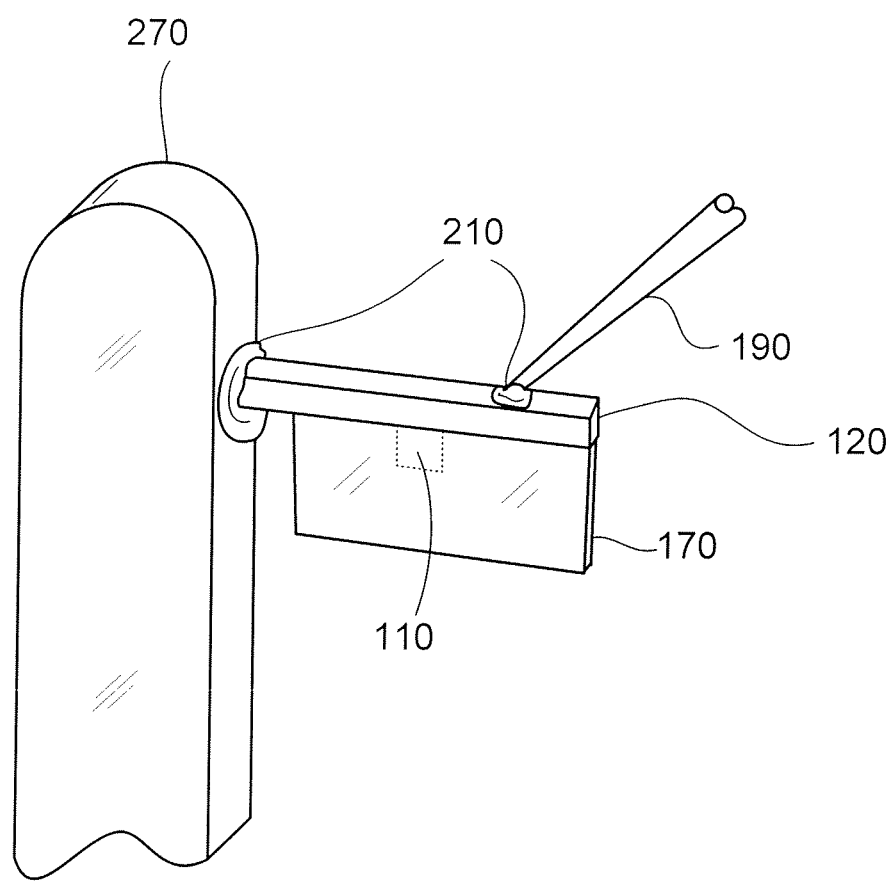
FIG. 9 shows an exemplary sample attached to a grid or holder for further analysis.

FIG. 9 is an exemplary illustration of attachment of the sample 170 to a holder 270, such as a TEM grid, for further thinning or analysis. The sample 170 (including the just-described wedge sample 175) may have been extracted from the substrate 100 by any of the embodiments shown previously. In FIG. 9, the attachment to the holder 270 is shown by CVD welding 210, although other methods known in the art could be used. Only the stress-buffer layer 120 should be attached to the holder 220 before the probe 190 is cut free, so that stresses on the sample 170 are greatly reduced.

None of the description in this application should be read as implying that any particular element, step, or function is an essential element which must be included in the claim scope; the scope of patented subject matter is defined only by the allowed claims. Moreover, none of these claims are intended to invoke paragraph six of 35 U.S.C. Section 112 unless the exact words "means for" are used, followed by a gerund. The claims as filed are intended to be as comprehensive as possible, and no subject matter is intentionally relinquished, dedicated, or abandoned.

We claim:

1. A method for sample extraction in an energetic-beam instrument, comprising:
    positioning a substrate having a region of interest in the energetic-beam instrument; the region of interest comprising first and second sides;
    forming a stress-buffer layer on the substrate over the region of interest, where the stress-buffer layer extends in at least one dimension beyond the region of interest;
    cutting with the energetic beam a first cut into the substrate on the first side of the region of interest;
    cutting with the energetic beam a second cut into the substrate on the second side of the region of interest; and,
    cutting with the energetic beam an isolating cut into the substrate, whereby the region of interest is isolated from the substrate but remains attached to at least a portion of the stress-buffer layer.

2. The method of claim 1, further comprising attaching an end-effector of a nano-manipulator to the stress-buffer layer.

3. The method of claim 2, where attaching of the end-effector to the stress-buffer layer comprises attaching the probe of a nano-manipulator by gas-assisted deposition.

4. The method of claim 2, further comprising:
cutting the stress-buffer layer after attachment of the end-effector to the stress-buffer layer, so as to completely free a sample from the substrate.

5. The method of claim 4, further comprising attaching a portion of the stress-buffer layer attached to the freed sample to a holder.

6. The method of claim 5 further comprising removing the attachment of the end-effector to the stress-buffer layer of the freed sample.

7. The method of claim 5, where the holder comprises a TEM grid.

8. The method of claim 1, further comprising making the isolating cut at least partially into the stress-buffer layer.

9. The method of claim 1, where the stress-buffer layer also comprises a protective layer.

10. The method of claim 1, where the stress-buffer layer is formed in addition to a protective layer.

11. A method for sample extraction in an energetic-beam instrument, comprising:
positioning a substrate having a region of interest in the energetic-beam instrument; the region of interest comprising first and second sides;
forming a stress-buffer layer on the substrate adjacent to the region of interest;
cutting with the energetic beam a first cut into the substrate on the first side of the region of interest;
cutting with the energetic beam a second cut into the substrate on the second side of the region of interest; and,
cutting with the energetic beam an isolating cut into the substrate, whereby the region of interest and a portion of the substrate is isolated from the remainder of the substrate, but remains attached to at least a portion of the stress-buffer layer by the portion of the substrate isolated along with the region of interest.

12. The method of claim 11, further comprising attaching an end-effector of a nano-manipulator to the stress-buffer layer.

13. The method of claim 12, where attaching of the end-effector to the stress-buffer layer comprises attaching the probe of a nano-manipulator by gas-assisted deposition.

14. The method of claim 12, further comprising:
cutting the stress-buffer layer after attachment of the end-effector to the stress-buffer layer, so as to completely free a sample from the substrate.

15. The method of claim 14, further comprising attaching a portion of the stress-buffer layer attached to the freed sample to a holder.

16. The method of claim 15 further comprising removing the attachment of the end-effector to the stress-buffer layer of the freed sample.

17. The method of claim 15, where the holder comprises a TEM grid.

18. The method of claim 11, further comprising making the isolating cut at least partially into the stress-buffer layer.

19. The method of claim 11, where the stress-buffer layer also comprises a protective layer.

20. The method of claim 11, where the stress-buffer layer is formed in addition to a protective layer.

21. A method for sample extraction in an energetic-beam instrument, comprising:
positioning a substrate having a region of interest in the energetic-beam instrument;
forming a stress-buffer layer of a known minimum height on the substrate, where the stress-buffer layer extends in at least one dimension beyond the region of interest;
cutting with the energetic beam a first cut into the substrate at substantially normal incidence to the plane of the substrate;
cutting with the energetic beam a second cut into the substrate at an angle of incidence less than 90 degrees to the plane of the substrate so that the region of interest is isolated from the substrate but remains attached to at least a portion of the stress-buffer layer.

* * * * *